(12) United States Patent
Matsumoto et al.

(10) Patent No.: US 8,437,828 B2
(45) Date of Patent: May 7, 2013

(54) BLOOD INSPECTION DEVICE

(75) Inventors: Toshiki Matsumoto, Ehime (JP);
Toshihiro Akiyama, Kanagawa (JP)

(73) Assignee: Panasonic Corporation, Osaka (JP)

( * ) Notice: Subject to any disclaimer, the term of this patent is extended or adjusted under 35 U.S.C. 154(b) by 859 days.

(21) Appl. No.: 12/523,389

(22) PCT Filed: Jan. 16, 2008

(86) PCT No.: PCT/JP2008/050440
§ 371 (c)(1),
(2), (4) Date: Jul. 16, 2009

(87) PCT Pub. No.: WO2008/087982
PCT Pub. Date: Jul. 24, 2008

(65) Prior Publication Data
US 2010/0030037 A1    Feb. 4, 2010

(30) Foreign Application Priority Data
Jan. 17, 2007  (JP) ................................ 2007-007755

(51) Int. Cl.
*A61B 5/05*  (2006.01)
*A61B 5/00*  (2006.01)
*A61B 17/32* (2006.01)

(52) U.S. Cl.
USPC ............ 600/345; 600/309; 600/573; 606/167

(58) Field of Classification Search .......... 600/345–361; 606/9, 167–189
See application file for complete search history.

(56) References Cited

U.S. PATENT DOCUMENTS

| 5,047,044 | A | * | 9/1991 | Smith et al. ................... 606/182 |
| 5,593,390 | A | * | 1/1997 | Castellano et al. ........... 604/187 |
| 5,725,747 | A | * | 3/1998 | Pinkowski et al. ........... 204/415 |
| 5,993,439 | A | * | 11/1999 | Costello et al. ................ 606/9 |
| 6,074,383 | A | * | 6/2000 | Grippi et al. ................... 606/14 |
| 6,197,040 | B1 | * | 3/2001 | LeVaughn et al. ............ 606/182 |
| 6,233,269 | B1 | * | 5/2001 | Lohrding et al. ............. 372/109 |
| 6,733,493 | B2 | | 5/2004 | Gruzdev et al. |
| 7,113,875 | B2 | | 9/2006 | Terashima et al. |

(Continued)

FOREIGN PATENT DOCUMENTS

| JP | 2001-170031 | 6/2001 |
| JP | 2003-265444 | 9/2003 |
| JP | 2003-287534 | 10/2003 |
| JP | 2004-533866 | 11/2004 |

OTHER PUBLICATIONS

English language Abstract of JP 2004-533866, Nov. 11, 2004.
English language Abstract of JP 2003-287534, Oct. 10, 2003.

(Continued)

*Primary Examiner* — Navin Natnithithadha
*Assistant Examiner* — Meredith Weare
(74) *Attorney, Agent, or Firm* — Greenblum & Bernstein, P.L.C.

(57) ABSTRACT

A blood inspection device capable of separately discharging a sensor and a filter by using a single discharger means. The blood inspection device has a housing provided with a circular hollow cylindrical body having an opening. A filter including a filter is provided inside the cylindrical body, and a sensor is provided outside the cylindrical body. A body of the discharger is slidable outside the cylindrical body. A first discharge section of the discharge comes into contact with the sensor unit to push out and discharge it. A second discharge section of the discharger comes into contact with the filter to push out and discharge it.

24 Claims, 16 Drawing Sheets

U.S. PATENT DOCUMENTS

| | | |
|---|---|---|
| 7,524,317 B2 | 4/2009 | Gruzdev et al. |
| 2002/0058953 A1 | 5/2002 | Gruzdev et al. |
| 2002/0198444 A1* | 12/2002 | Uchigaki et al. .............. 600/345 |
| 2003/0144608 A1* | 7/2003 | Kojima et al. ................ 600/583 |
| 2003/0187589 A1 | 10/2003 | Terashima et al. |
| 2004/0127815 A1* | 7/2004 | Marchitto et al. ............ 600/573 |
| 2004/0210279 A1 | 10/2004 | Gruzdev et al. |
| 2005/0011759 A1* | 1/2005 | Moerman et al. ........ 204/403.03 |
| 2005/0224345 A1* | 10/2005 | Taniike et al. ........... 204/403.01 |
| 2005/0245844 A1* | 11/2005 | Mace et al. ................... 600/583 |
| 2007/0249963 A1* | 10/2007 | Alden et al. ................... 600/583 |
| 2008/0064941 A1* | 3/2008 | Funderburk et al. .......... 600/347 |
| 2009/0043227 A1 | 2/2009 | Fujiwara et al. |
| 2009/0177117 A1 | 7/2009 | Amano et al. |

OTHER PUBLICATIONS

English language Abstract of JP 2003-265444, Sep. 24, 2003.
English language Abstract of JP 2001-170031, Jun. 26, 2001.

* cited by examiner

BLOOD INSPECTION DEVICE

TECHNICAL FIELD

The present invention relates to a blood test apparatus that tests the property of blood and the like.

BACKGROUND ART

Diabetes patients need to measure their blood sugar level on a regular basis and inject insulin based on this measured blood sugar level to maintain a normal blood sugar level. To maintain this normal blood sugar level, diabetes patients need to measure the blood sugar level on a regular basis, and sample a small amount of blood from their fingertips using a blood test apparatus and measure the blood sugar level from the sampled blood.

As shown in FIG. 1, a conventional blood test apparatus is formed with: housing 2; cylindrical body 2a that forms this housing 2; opening part 2c that forms the front end of this cylindrical body 2a; laser emitting apparatus 3 that is provided in housing 2; blood sensor 4 (hereinafter, "sensor") that is attached facing this laser emitting apparatus 3; electrical circuit section 5 that is connected to this blood sensor 4; and filter 6 that is provided between laser emitting apparatus 3 and blood sensor 4 and that allows laser light 3a to pass.

The operation of blood test apparatus 1 constituted as described above will be explained below. First, sensor 4 and filter 6 that are not used yet are attached. Then, as shown in FIG. 2, blood test apparatus 1 is abutted on skin 9 of the left hand using, for example, the right hand. Next, puncturing button 3b shown in FIG. 1 is pressed. Then, laser emitting apparatus 3 emits laser light 3a. Laser light 3a passes filter 6 and sensor 4 and punctures skin 9 (see FIG. 2). By this puncturing, blood 10 flows out from skin 9. This blood 10 is detected by sensor 4. Then, electrical circuit section 5 provided in blood test apparatus 1 measures the blood sugar level. After the measurement of the blood sugar level is finished, sensor 4 is removed and discarded. Further, filter 6 is separately removed depending on how dirty filter 6 is and is discarded.

Furthermore, for example, Patent Document 1 and Patent Document 2 are known as prior art reference information related to the present invention. Patent Document 2 discloses an example of a conventional blood test apparatus of an optical reading measurement type (without a filter).
Patent Document 1: Japanese Translation of PCT Application Laid-Open No. 2004-533866
Patent Document 2: Japanese Patent Application Laid-Open No. 2001-170031

DISCLOSURE OF INVENTION

Problems to be Solved by the Invention

However, with such conventional blood test apparatuses, sensor 4 and filter 6 are attached in different locations or a filter itself is not attached. Therefore, there is a possibility that, when a filter is not attached, dust from the surrounding, blood and so on enter inside the blood test apparatus and cause a problem, or, even when a filter is attached, dust from the surrounding, blood and so on adhere to filter 6. Further, in case of laser puncturing, dirt is likely to adhere to the vicinity of the part to puncture, because of the substance (i.e. the substance produced when skin transpires) produced by the transpiration of skin radiated by laser light. Therefore, when filter 6 is dirty, sensor 4 must be removed and, further, filter 6 attached in a different location must also be removed. That is, sensor 4 and filter 6 must be removed separately, which is troublesome, and there are many structures of blood test apparatuses from which filters cannot be removed easily and maintenance of these blood test apparatuses is not easy.

It is therefore an object of the present invention to provide a blood test apparatus that solves the above-described problem and that can easily eject a sensor unit including the blood sensor and a filter unit including the filter.

Means for Solving the Problem

To achieve this object, the blood test apparatus according to the present invention can eject the sensor unit and the filter unit separately using a single ejecting means. Consequently, it is possible to achieve the desired object.

Advantageous Effect of the Invention

The present invention can eject the sensor unit and the filter unit separately using a single ejecting means and can eject the sensor unit and the filter unit only by operating a single ejecting means. Accordingly, it is not necessary to remove the sensor unit and filter unit from separate locations, thereby making the ejection substantially easy.

Further, by replacing only the blood sensor after puncturing, it is possible to measure a plurality of other items (glucose+lactate acid and so on) in bodily fluid such as blood.

BEST MODE FOR CARRYING OUT THE INVENTION

Hereinafter, embodiments of the present invention will be explained based on the accompanying drawings.

Embodiment 1

Figure 3:
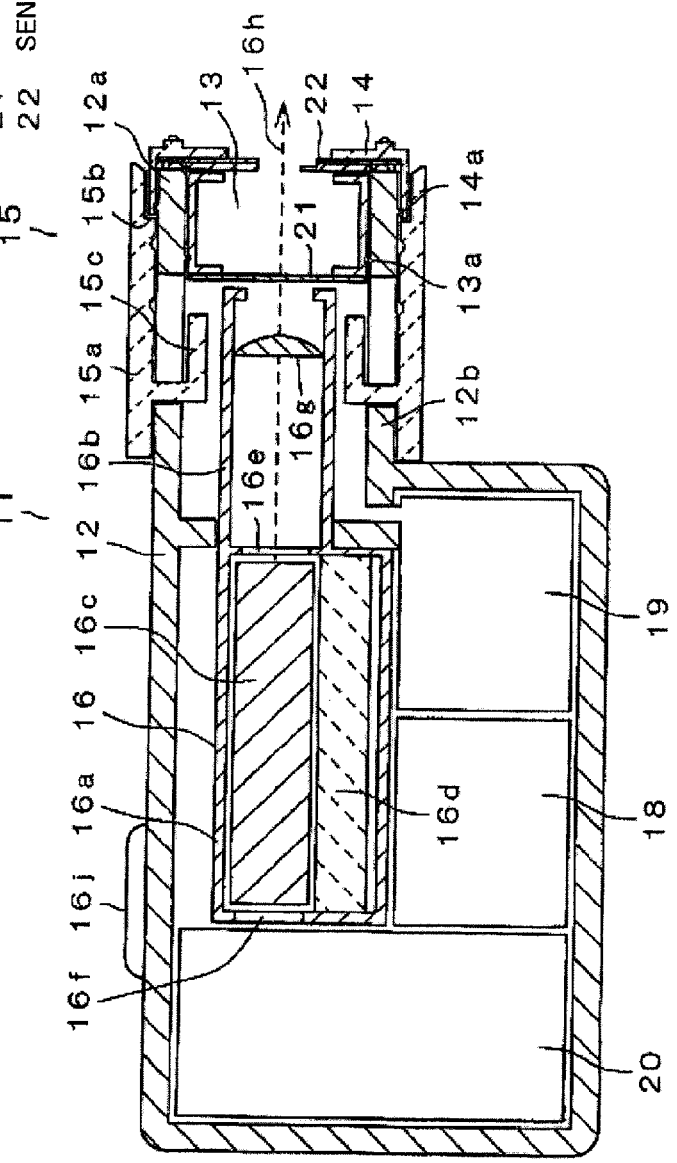
FIG. 3 is a cross-sectional view of a blood test apparatus according to Embodiment 1 of the present invention.

FIG. 3 is a cross-sectional view of blood test apparatus 11 according to Embodiment 1 of the present invention. In FIG. 3, housing 12 is made of a resinic material and is provided with cylindrical body 12b of a cylindrical shape that has opening part 12a. Filter unit 13 including filter 21 is attached inside cylindrical body 12b and sensor unit 14 including sensor 22 for analyzing the components of bodily fluid such as blood, is attached on the outer surface of cylindrical body 12b.

Body part 15a of ejecting means 15 is provided slidably on the outer surface of cylindrical body 12b. First ejecting part 15b and second ejecting parts 15c are formed in body part 15a. First ejecting part 15b abuts on sensor unit 14 to push out and eject sensor unit 14. Further, second ejecting parts 15c abut on filter unit 13 to push out and eject filter unit 13.

Next, laser emitting apparatus 16 provided in housing 12 will be explained. This laser emitting apparatus 16 is constituted by oscillating tube 16a and cylindrical body 16b of a cylindrical shape coupled to the front of this oscillating tube 16a. Oscillating tube 16a accommodates Er:YAG (yttrium aluminum garnet) laser crystal 16c and flash light source 16d. Partial transmission mirror 16e of about one percent transmittance is attached to one end of oscillating tube 16a, and total reflection mirror 16f is attached to the other end. Convex lens 16g is attached in cylindrical body 16b ahead of partial transmittance mirror 16e and is set to adjust a focus of laser light emitted from laser crystal 16c under the skin of the patient.

Figure 1:
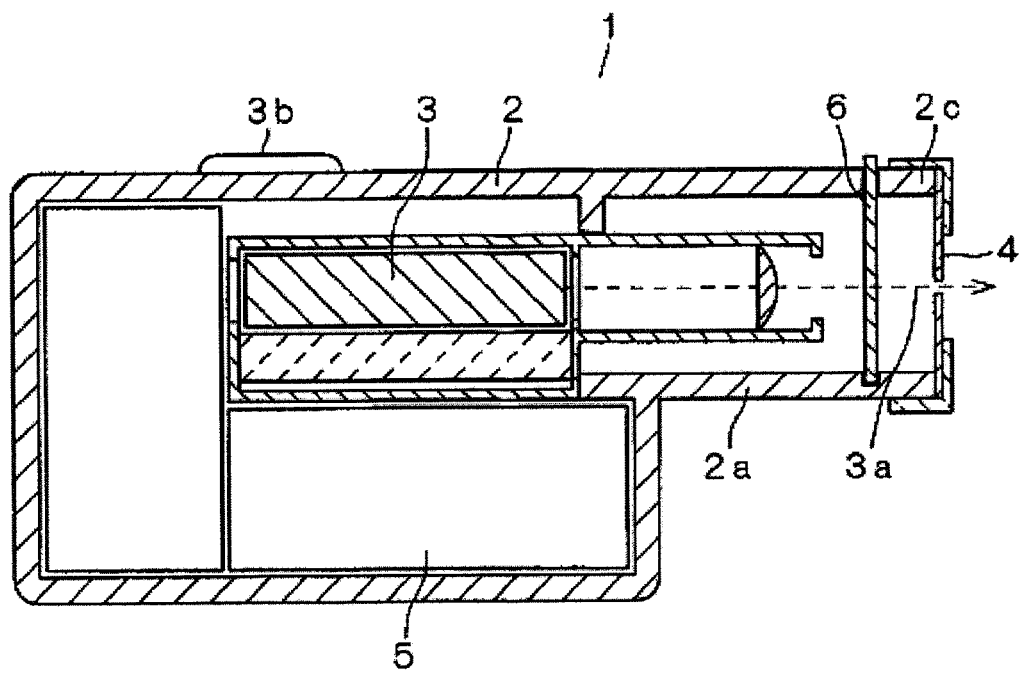
FIG. 1 is a cross-sectional view of a conventional blood test apparatus.
Figure 2:
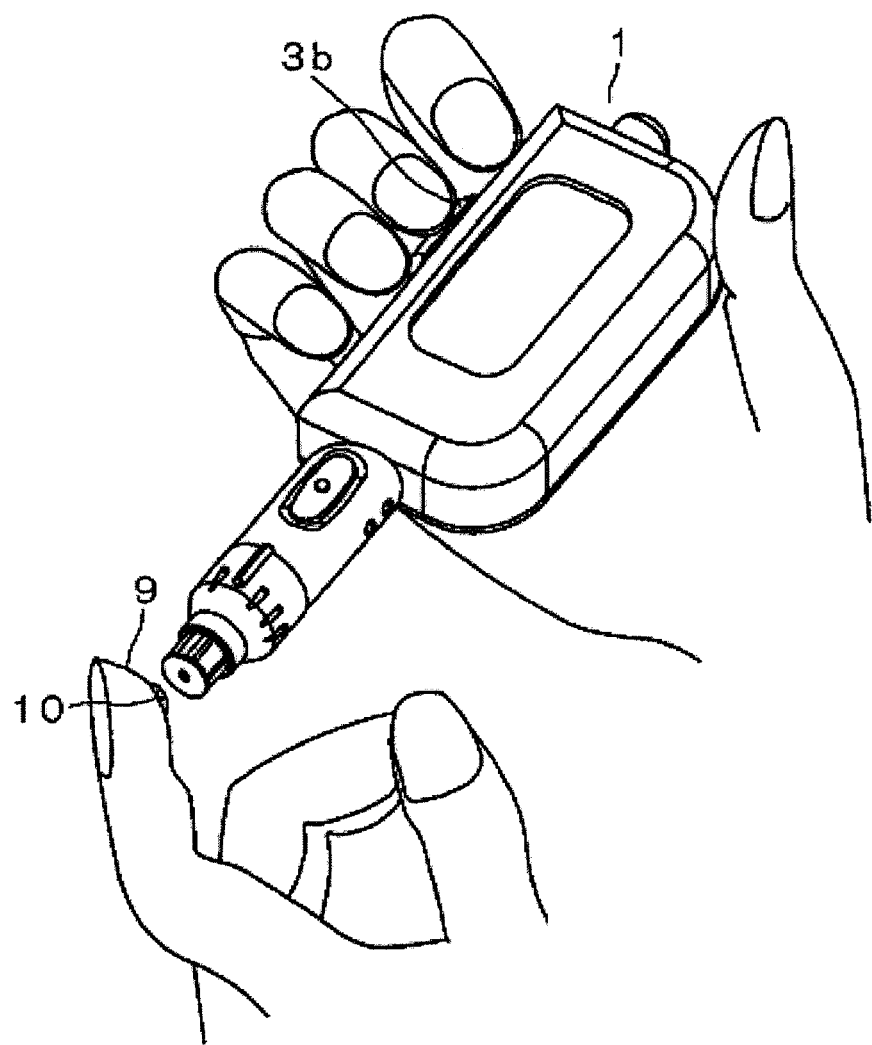
FIG. 2 illustrates the state of use of the conventional blood test apparatus.

Electrical circuit section 18 is connected to sensor 22 forming sensor unit 14 through connectors 53 (see FIG. 4 and this will be described later) and measures the blood sugar level from blood 10 (see FIG. 2) taken in sensor 22. Vacuuming means 19 applies a negative pressure to the vicinity of sensor 22 and lifts up skin 9 upon puncturing to make it easier to sample blood. Battery 20 supplies power to electrical circuit section 18 and laser emitting apparatus 16.

The operation of blood test apparatus 11 constituted as described above will be explained below. First, prior to test of blood 10 (see FIG. 2), the user (i.e. patient) inserts filter unit 13 inside cylindrical body 12b to make locking parts 13a lock filter unit 13. Next, the user fits sensor unit 14 onto the outer surface of cylindrical body 12b to make locking parts 14a lock sensor unit 14. At this time, connectors 53 (see FIG. 4) provided with opening part 12a contact connection electrodes provided in sensor 22 to electrically connect sensor 22 and electrical circuit section 18.

Next, the user makes blood test apparatus 11 abut on skin 9 to sample blood. Then, the user presses start button 16j. Then, flash light source 16d emits light, and the light source emitted from this flash light source 16d enters Er:YAG laser crystal 16c and the crystal is excited to generate laser light. Further, laser light is reflected between total reflection mirror 16f, YAG laser crystal 16c and partial transmission mirror 16e to oscillate and amplify. Part of this amplified laser light passes partial transmission mirror 16e by stimulated emission. Laser light 16h that has passed this partial transmission mirror 16e passes lens 16g to emit and its focus is adjusted inside skin 9. Preferably, the depth of the focus laser light punctures skin is between 0.1 millimeters and 1.5 millimeters from skin 9, and is 0.5 millimeters with the present embodiment.

Blood 10 flows out from punctured skin 9. Blood 10 that has flowed out is taken in sensor 22 and causes a chemical reaction in this sensor 22. Information about blood 10 that causes the chemical reaction is transmitted to electrical circuit section 18 through the connectors and the blood sugar level and the like is measured in electrical circuit section 18. Further, details of this will be explained later. After the blood sugar level and the like is measured, the user ejects sensor unit 14 that has been used. Further, when filter 21 is dirty, the user also ejects filter unit 13 using ejecting means 15. How this ejection is performed will be explained next.

First, the user moves body part 15a of ejecting means 15 toward opening part 12a. Then, first ejecting part 15b presses against sensor unit 14 and releases the lock in locking parts 14a. Then, first ejecting part 15b ejects sensor unit 14 from cylindrical body 12b and stops.

Further, when filter 21 becomes dirty due to, for example, scattering blood 10 and skin 9, the user further moves body part 15a toward opening part 12a. By so doing, second ejecting parts 15c press against filter unit 13 and release the lock in locking parts 13a. Then, second rejecting parts 15c eject filter unit 13 from cylindrical body 12b and stop.

In this way, only by operating body part 15a, it is possible to separately eject sensor unit 14 and filter unit 13 that have been used. Consequently, sensor unit 14 and filter unit 13 are ejected substantially easily.

Further, by replacing only sensor unit 14 a plurality of times after puncturing, it is possible to measure other items (glucose+lactate acid and so on) in bodily fluid such as blood or interstitial fluid.

With the present embodiment, laser emitting apparatus 16 that can puncture skin 9 of the patient without contacting his skin, so that the operation of replacing the puncturing needle is not required compared to a contact type puncturing apparatus that uses a puncturing needle, and preparation before puncturing is simplified significantly. Further, skin 9 and laser emitting apparatus 16 do not contact, which is sanitary. Furthermore, there are no movable components unlike puncturing apparatuses that use a puncturing needle and the number of components decreases. Accordingly, an accident takes place less and it is easy to manage the components. Moreover, the structure of blood test apparatus 11 can be made waterproof, so that the apparatus can be washed entirely. Further, the puncturing voltage for this laser light 16h is about 300 volts. Accordingly, patients suffer from little pain.

Figure 4:
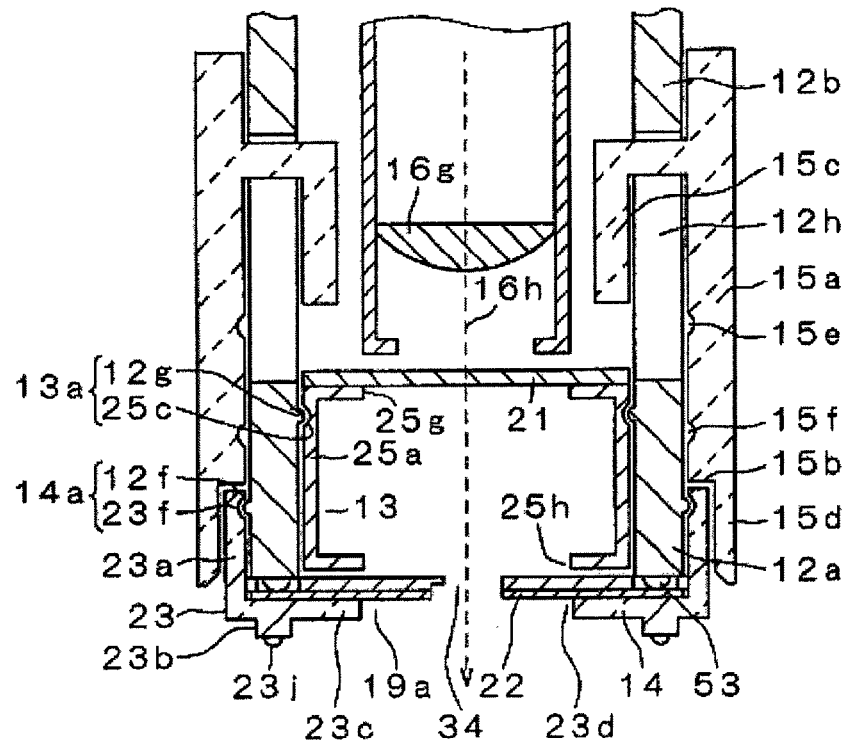
FIG. 4 is a cross-sectional view of main parts in the blood test apparatus according to Embodiment 1 of the present invention in the first state seen from the side.

Filter unit 13, sensor unit 14 and ejecting means 15 will be further explained in detail below. FIG. 4 is a cross-sectional view showing the vicinity of filter unit 13 and sensor unit 14 used in blood test apparatus 11 seen from the side, and FIG. 5 is a cross-sectional view showing filter unit 13 and sensor unit 14 seen from above.

Figure 5:
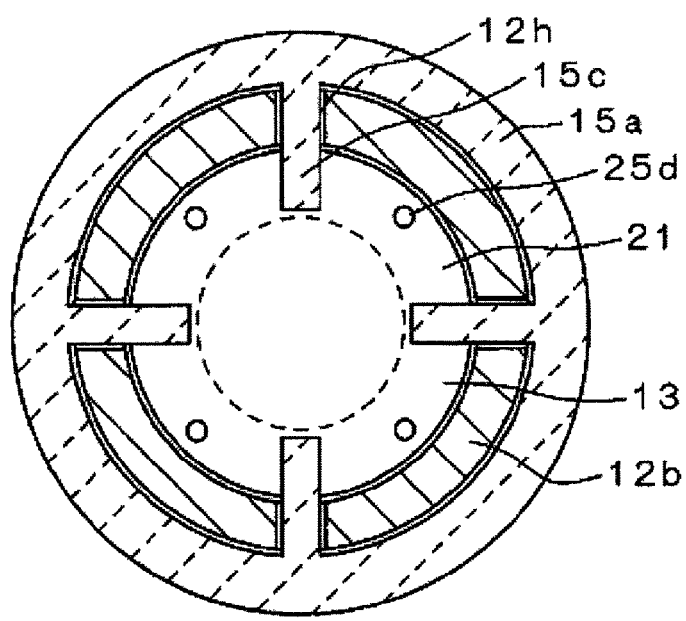
FIG. 5 is a cross-sectional view of the blood test apparatus according to Embodiment 1 of the present invention seen from above.

In FIG. 4 and FIG. 5, sensor unit 14 is made of a resinic material and constituted by cylindrical holder 23 that is open at both ends and sensor 22 that is attached to this holder 23. Holder 23 is integrally formed with: cylindrical upper part 23a; cylindrical lower part 23b of a smaller diameter than this upper part 23a; and circular, disc-shaped receiving part 23c, which partitions between this lower part 23b and upper part 23a, and on which sensor 22 is arranged. The diameter of lower part 23b is made smaller than upper part 23a to allow a plurality of holders 23 to be stacked in layers and accommodated and adopts dimensions to allow lower part 23b of second holder 23 to be inserted inside upper part 23a of first holder 23. Accordingly, it is possible to accommodate holders in small space because first holder 23 and second holder 23 are overlaid.

Further, positioning concave parts 23f making locking parts 14a between upper part 23a and cylindrical body 12b are formed in the inner surface of upper part 23a, and hole 23d is formed in the center of receiving part 23c. This hole 23d and the interior of lower part 23b form vacuuming chamber 19a. 23j are skin detecting sensors provided in the bottom surface of lower part 23b, and these skin detecting sensors 23j are conducted with the interior of holder 23 through conductors and connected with electrodes that are formed in positioning concave parts 23f.

These skin detecting sensors 23j are formed with two conductive electrodes provided in different locations in the bottom surface of lower part 23b and detect contact with skin 9 based on the change in the resistance value between conductive electrodes when these skin detecting sensors 23j abut on skin 9. Then, detection signals are communicated to electrical circuit section 18 through positioning concave parts 23f. Skin detecting sensors 23j in the present embodiment use conductive electrodes and, consequently, can be realized at low cost. Further, optical sensors, temperature sensors and the like can be used in addition to conductive electrodes for these skin detecting sensors 23j.

Next, filter unit 13 will be explained. Filter unit 13 is formed with cylindrical holder 25a made of resin and filter unit 21 attached on the upper surface of this holder 25a. This filter 21 is made of material such as glass or transparent resin (ex. polypropylene) that allows laser light to pass. Accordingly, filter 21 plays a role of allowing laser light 16h to pass and preventing, for example, the substance that has transpired and scattered from skin 9 upon puncturing, from adhering to lens 16g.

Further, filter 21 is attached on the upper surface of holder 25a, that is, closer to lens 16g than to sensor 22. Consequently, filter 21 is placed apart from the focus of laser light 16h and is protected from the energy of laser light 16h. Further, if filter 21 is provided apart from the focus of laser light 16h, for example, the amount of the substance that has transpired and scattered from skin 9 and adheres to filter 21, decreases. That is, filter 21 is prevented from being dirty, and the number of times filter 21 can be used increases, which is economical.

Circular hole 25h is provided above holder 25a forming filter unit 13 and circular hole 25h is provided below holder 25a. Laser light 16h passes filter 21, hole 25g, hole 25h and storing part 34 of sensor 22 and punctures skin 9.

Next, how filter unit 13 and sensor unit 14 are attached to cylindrical body 12b will be explained. In the outer surface of opening part 12a of cylindrical body 12b, positioning convex parts 12f are formed in the positions to meet positioning concave parts 23f provided in sensor unit 14. These positioning convex parts 12f make holder 23 fit onto the outer surface of cylindrical body 12b and is elastic so as to fit in positioning concave parts 23f.

In the inner surface of cylindrical body 12b, positioning convex parts 12g are formed in the positions to meet positioning concave parts 25c provided in filter unit 13. These positioning convex parts 12g insert holder 25a inside cylindrical body 12b and is elastic so as to fit in positioning concave parts 25c. Positioning concave parts 23f and positioning convex parts 12f make locking parts 14, and positioning concave parts 25c and positioning convex parts 12g make locking parts 13a. Consequently, when filter unit 13 is inserted inside cylindrical body 12b, positioning concave parts 25c and positioning convex parts 12g fit in locking parts 13a, and the position of filter unit 13 in cylindrical body 12b is determined. Then, when sensor unit 14 is fitted onto the outer surface of cylindrical body 12b, positioning concave parts 23f and positioning convex parts 12f fit in locking parts 14a, thereby determining the position of sensor unit 14 in cylindrical body 12b.

In the bottom surface of opening part 12a, connectors 53 (including connectors 53a to 53f), which will be described later, are provided, and these connectors 53 abut on connection electrodes 41a to 45a (described later) formed in sensor 22 when sensor unit 14 is attached to cylindrical body 12b. Accordingly, signals from connection electrodes 41a to 45a are supplied to electrical circuit section 18 through these connectors 53. Further, electrodes are also provided in the surfaces of positioning convex parts 12f and signals from skin detecting sensors 23j are supplied to electrical circuit section 18.

Next, ejecting means 15 will be explained. Body part 15a constituting ejecting means 15 is made of resin and is cylindrical. Further, body part 15a is provided so as to slidably move on the outer surface of cylindrical body 12b. In the lower portion of this body part 15a, first ejecting part 15b for pushing out the upper end of sensor unit 14 is formed. Further, cover part 15d that covers the outer surface of holder 23 is formed continuing from this first ejecting part 15b. The lower portion of this cover part 15d is tapered widening downward to make it easier to insert sensor unit 14.

From the inner surface of body part 15a, second ejecting parts 15c of a hook shape for pushing out filter unit 13 through holes 12h formed in cylindrical body 12b are provided every 90 degrees (see FIG. 5). Moreover, concave parts 15e and concave parts 15f are formed in portions of the inner surface of this body part 15a from the bases of second ejecting parts 15c to cover parts 15d. When sensor unit 14 is ejected, concave parts 15f fit in positioning convex parts 12f and stop. When body part 15a is further pushed out, concave parts 15e eject filter unit 13, and fit in positioning convex parts 12f and stop. As shown in FIG. 5, the negative pressure produced in vacuuming means 19 is supplied to vacuuming chamber 19a by providing holes 25d penetrating the top and bottom of filter 21. With the present embodiment, four holes 25d forming these vacuuming passages are formed. Further, body part 15a, cylindrical body 12b and holder 25a may be made of transparent members such that how dirty filter 21 is can be checked from the outside.

Figure 6:
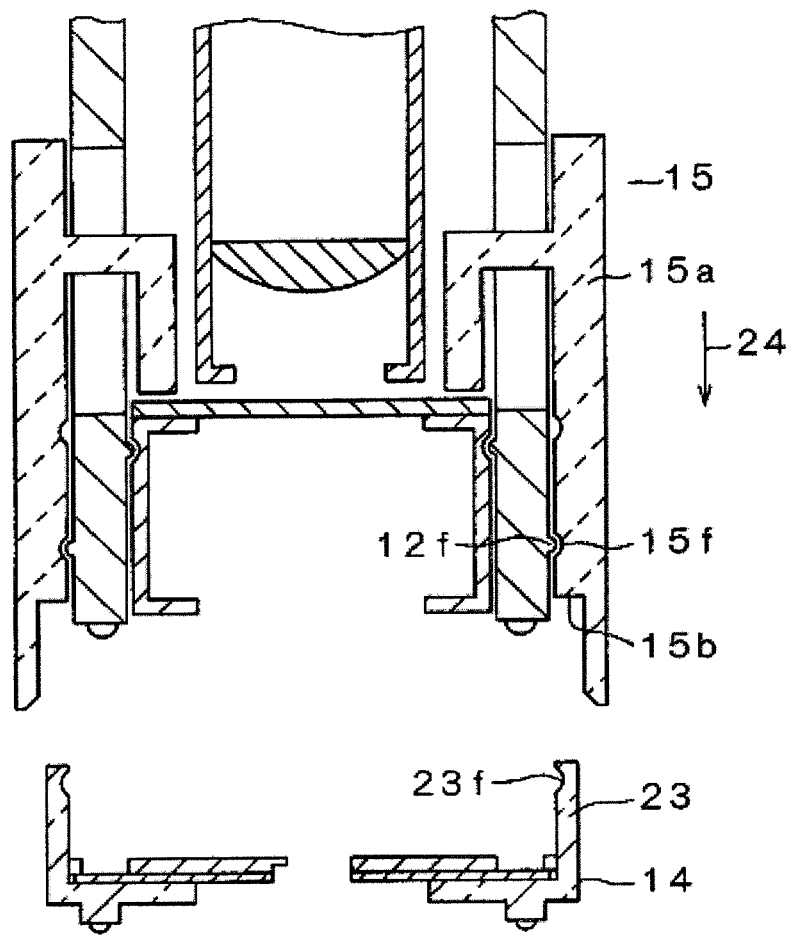
FIG. 6 is a cross-sectional view of main parts in the blood test apparatus according to Embodiment 1 of the present invention in the second state.
Figure 7:
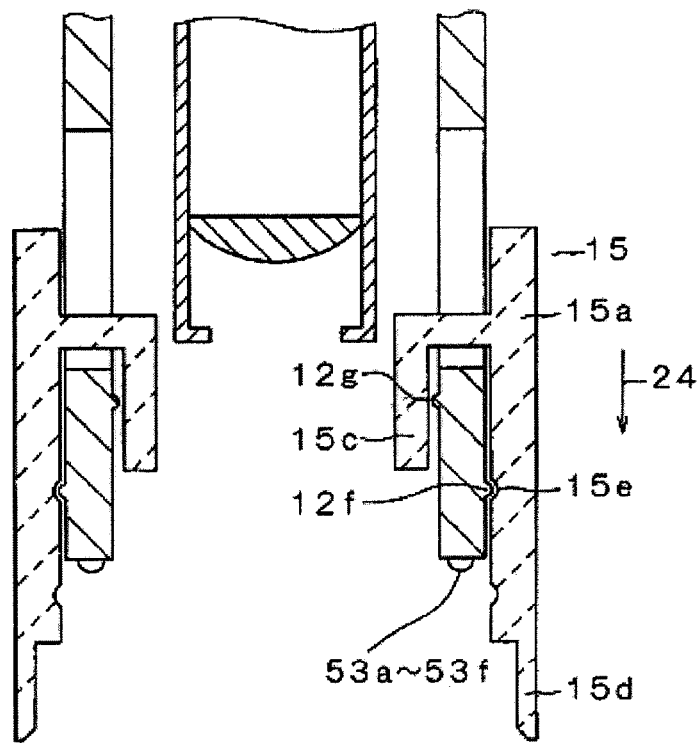
FIG. 7 is a cross-sectional view of main parts in the blood test apparatus according to Embodiment 1 of the present invention in the third state.
Figure 7:
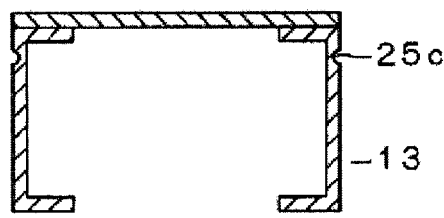

Next, ejection of sensor unit 14 will be explained using FIG. 6 and ejection of filter unit 13 will be explained using FIG. 7. FIG. 6 is a cross-sectional view of main parts after sensor unit 14 is ejected. Body part 15a of ejecting means 15 is moved in the direction of arrow 24 (toward opening part 12a). Then, first ejecting part 15b constituting ejecting means 15 releases the engagement between positioning concave parts 23f and positioning convex parts 12f to eject sensor unit 14. Concave parts 15f fit in positioning convex parts 12f and stop. Consequently, when filter 21 is not dirty very much, only sensor unit 14 can be replaced.

Next, body part 15a is further moved in the direction of arrow 24. Then, as shown in FIG. 7, second ejecting parts 15c release the engagement between positioning concave parts 25c and positioning convex parts 12g and further move in the direction of arrow 24, thereby ejecting filter unit 13. Next, concave parts 15e fit in positioning convex parts 12f and stop. Here, in a state where sensor unit 14 is ejected or in a state where filter unit 13 is ejected, cover part 15d provided at the front end of body part 15a goes down, so that this cover part 15d plays a role of protecting connectors 53a to 53f from dust and dirt.

Sensor unit 14 and filter unit 13 are attached in steps opposite to the above steps. That is, first, filter unit 13 is inserted inside cylindrical body 12b. Then, positioning concave parts 25c fit in positioning convex parts 12g forming locking parts 13a, thereby determining the position of filter unit 13. Next, sensor unit 14 shown in FIG. 6 is fitted onto the outer periphery of cylindrical body 12b. The upper end of holder 23 abuts on ejecting part 15b and pushes body part 15a upward. Then, positioning concave parts 23f fit in positioning convex parts 12f forming locking parts 14a, thereby determining the position of sensor unit 14.

Figure 8:
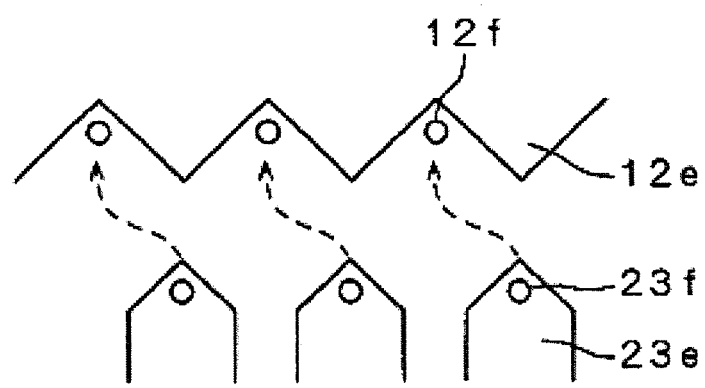
FIG. 8 is a developed plan view of guiding parts of the blood test apparatus according to Embodiment 1 of the present invention.

At this time, a device is made as follows such that connection electrodes 41a to 45a abut on connectors 53a to 53f even when cylindrical sensor unit 14 is inserted carelessly. That is, guides 23e shown in FIG. 8 are formed in the inner surface of upper part 23a of holder 23 constituting sensor unit 14. Further, guides 12e are formed in the outer surface of cylindrical body 12b onto which this sensor unit 14 is fitted. Consequently, even when cylindrical sensor unit 14 is inserted carelessly, guides 23e are inserted along guides 12e of cylindrical body 12b, so that it is possible to make connection electrodes 41a to 45a abut on connectors 53a to 53f in a reliable manner. These connectors 53a to 53f are directly provided in opening part 12a and need not to be moved to abut on connection electrodes 41a to 45a. Consequently, connectors 53a to 53f are electrically connected in a reliable manner and are mechanically simple, so that they produce little friction, thereby realizing electrical and mechanical reliability in connection parts.

As explained above, according to the present embodiment, it is possible to eject sensor unit 14 and filter unit 13 in two steps or eject them separately by moving body part 15a forming ejecting means 15. Accordingly, when filter 21 is not dirty so much, only sensor unit 14 may be ejected and, when filter 21 is very dirty, sensor unit 14 and filter unit 13 may be ejected together.

Further, these units are individual units and are easily attached and removed. Furthermore, even when one of sensor unit 14 and filter unit 13 is defective, the other good unit can be used and is not wasted.

Still further, ejecting means 15 according to the present embodiment ejects sensor unit 14 and then ejects filter unit 13, so that, when sensor 22 is defective for example, it is possible to replace only sensor 22 easily. It is possible to measure a plurality of other items (glucose+lactate acid and so on) in bodily fluid such as blood and interstitial fluid, by replacing only sensor 22 after puncturing, so that filter unit 13 is not wasted.

Moreover, to prevent blood test apparatus 11 from being used in a irregular state, detecting sensors for detecting whether or not filter unit 13 and sensor unit 14 are attached are provided to enable puncturing only when filter unit 13 and sensor unit 14 are attached.

Figure 9:
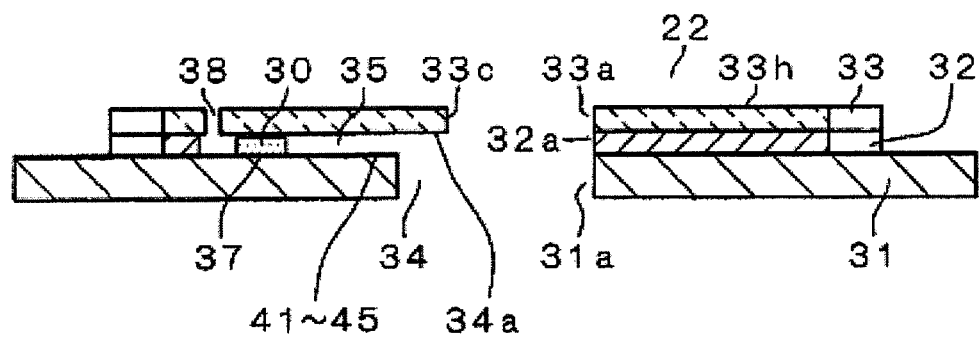
FIG. 9 is a cross-sectional view of a sensor of the blood test apparatus according to Embodiment 1 of the present invention.

FIG. 9 is a cross-sectional view of sensor 22 attached to sensor unit 14. This sensor 22 is constituted by: substrate 31; spacer 32 pasted on the upper surface of this substrate 31; and cover 33 pasted on the upper surface of spacer 32, and has a plate shape.

Substrate hole 31a formed in virtually the center of substrate 31, spacer hole 32a formed in virtually the center of spacer 32 and cover hole 33a formed in virtually the center of cover 33 communicate to form blood storing part 34.

This storing part 34 is open downward to abut on skin 9 and sample blood 10. One end of supply channel 35 continues to this storing part 34 and supply channel 35 leads blood 10 stored in storing part 34 by capillary action to detecting section 37 arranged on supply channel 35 (see FIG. 10). Further, the other end of this supply channel 35 continues to air hole 38.

Here, a water-repellant material is used for upper surface 33h of cover 33. Further, a hydrophillic material is used in supply channel 35. Here, preferably, ceiling 34a of storing part 34 is treated to be less hydrophilic than supply channel 35 or treated to be less water-repellant than upper surface 33h of cover 33.

Reagent 30 is arranged on detecting section 37. This reagent 30 can be formed by dropping and drying reagent 30 on detection electrodes 41 and 43 (see FIG. 10) formed in substrate 31.

Figure 10:
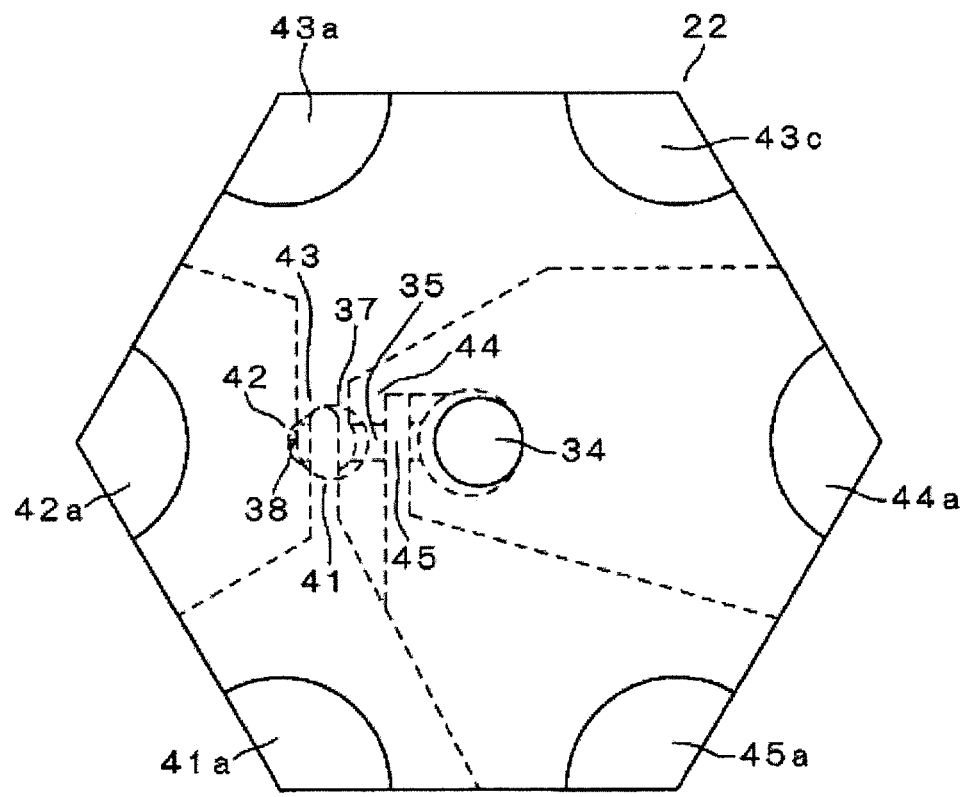
FIG. 10 is a perspective plan view of the sensor of the blood test apparatus according to Embodiment 1 of the present invention.

FIG. 10 is a perspective plan view of sensor 22. The shape of sensor 22 is a regular hexagon, and connection electrodes 41a to 45a that are connected with connectors 53a to 53f provided in opening part 12a of blood test apparatus 11 and reference electrode 43c that is connected with connection electrode 43a, are formed in respective six apexes of this regular hexagon.

Storing part 34 is provided in virtually the center of sensor 22, and supply channel 35, one end of which is connected with this storing part 34, is provided continuing to detection electrode 42. Further, the other end of this supply channel 35 continues to air hole 38. On this supply channel 35, there are, from the side closer to storing part 34, detection electrode 44 connected with connection electrode 44a, detection electrode 45 connected with connection electrode 45a, detection electrode 44, which is provided again, connected with connection electrode 44a, detection electrode 43 connected with connection electrode 43a and reference electrode 43c, detection electrode 41 connected with connection electrode 41a, detection electrode 43, which is provided again, connected with connection electrode 43a and reference electrode 43c and detection electrode 42 connected with connection electrode 42a. Further, reagent 30 (see FIG. 9) is arranged on detection electrodes 41 and 43.

Figure 11:
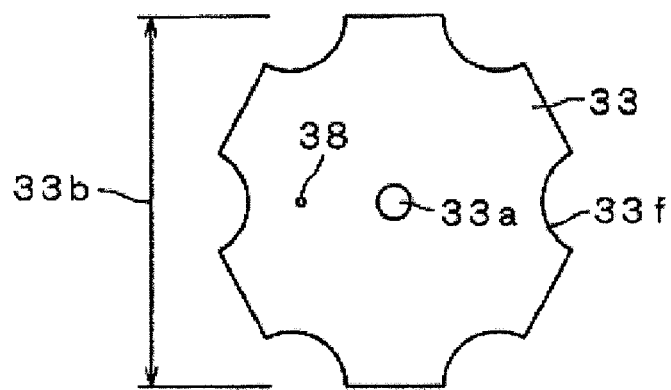
FIG. 11 is a plan view of components constituting the sensor of the blood test apparatus according to Embodiment 1 of the present invention, (a) is a plan view of a cover of the blood test apparatus according to Embodiment 1 of the present invention, (b) is a plan view of a spacer of the blood test apparatus according to Embodiment 1 of the present invention and (c) is a plan view of a substrate of the blood test apparatus according to Embodiment 1 of the present invention.
Figure 11:
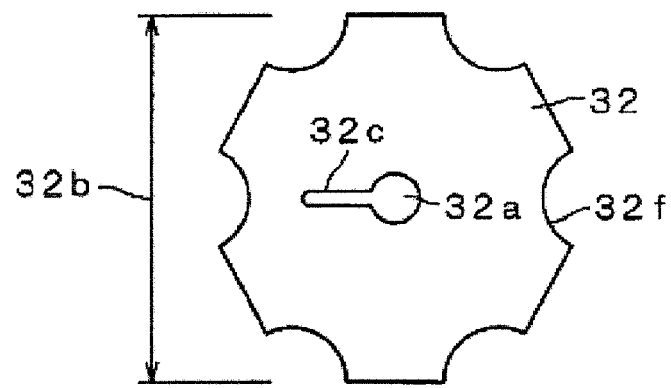
Figure 11:
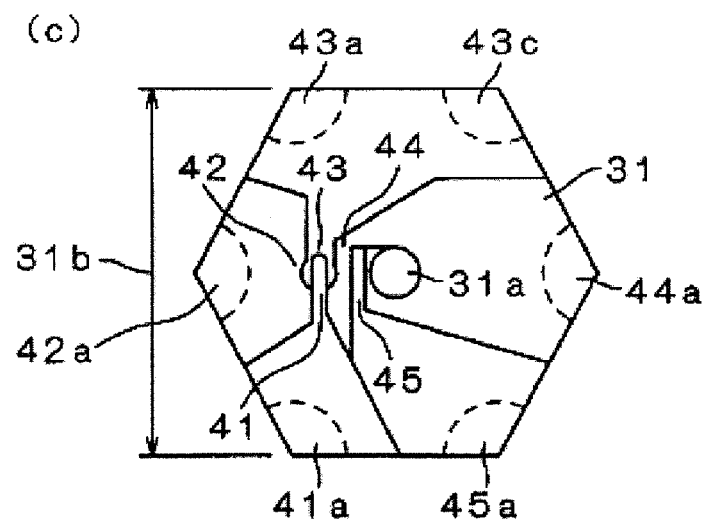

FIG. 11 is an exploded plan view of sensor 22. FIG. 11(c) is a plan view of regular hexagonal substrate 31 constituting sensor 22 and its dimension 31b is about 9 millimeters. The essential requirement is that the material of this substrate 31 is polyethylene terephthalate (PET) and the thickness of substrate 31 is about 0.1 millimeters.

The conductive layer is formed on the upper surface of this substrate 31 by the sputtering method or the vapor deposition method using metal material such as gold, platinum, or palladium, and detection electrodes 41 to 45 and connection electrodes 41a to 45a and reference electrode 43c derived from these detection electrodes 41 to 45 are integrally formed by applying laser machining to this conductive layer. Substrate hole 31a is provided in virtually the center of substrate 31.

FIG. 11(b) is a plan view of spacer 32 and its dimension 32b is about 9 millimeters. Spacer hole 32a is provided in virtually the center of spacer 32 in a position to meet substrate hole 31a. This spacer 32 is a regular hexagon, and six semicircular notches 32f are formed in the six apexes of this regular hexagon to meet connection electrodes 41a to 45a and reference electrode 43c of substrate 31.

Further, slit 32c is formed continuing to this spacer hole 32a and this slit 32c forms supply channel 35 for blood 10. The wall surfaces of this slit 32c and the upper surface of substrate 31 to meet the wall surfaces of slit 32c are subjected to hydrophilic treatment. The width of this slit 32c is made about 0.6 millimeters and the length of slit 32c is made about 2.5 millimeters to form supply channel 35 with a cavity of about 0.15 microliters. In this way, it is possible to perform test with a small amount of blood 10, so that patients do not have to get strained and scared. The material of spacer 32 is polyethylene terephthalate and the thickness of spacer 32 is about 0.05 millimeters.

FIG. 11(a) is a plan view of cover 33. Its dimension 33b is about 9 millimeters. 33a is a cover hole provided in a position slightly decentered from the center of cover 33. Air hole 38 is provided to meet the front end part of supply channel 35. Diameter 38a of this air hole 38 is about 50 micrometers. The reason for reducing the diameter of air hole 38 in this way is to prevent blood 10 from flowing out from air hole 38. Cover 33 is a regular hexagon, and six semicircular notches 33f are formed in the six apexes of this regular hexagon to meet connection electrodes 41a to 45a and reference electrode 43c of substrate 31. The material of this cover 33 is polyethylene terephthalate and the thickness of cover 33 is about 0.1 millimeters.

Substrate 31, spacer 32 and cover 33 constituting sensor 22 can be formed by dividing a parent substrate of a fixed measure into several pieces. These substrate 31, spacer 32 and cover 33 that are divided are regular hexagons and, consequently, can be aligned in the parent substrate without space. Accordingly, these materials are efficiently scribed in the parent substrate, which cuts waste, is economical and contributes to resource saving.

Further, the shape of sensor 22 may be a polygon other than a regular hexagon.

Figure 12:
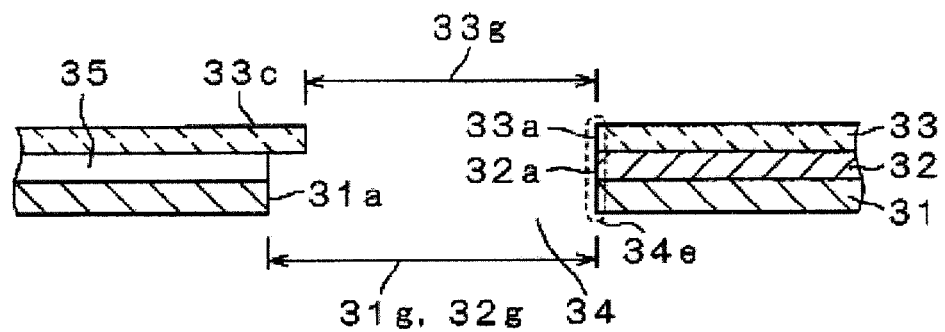
FIG. 12 is a cross-sectional view of main parts in the sensor of the blood test apparatus according to Embodiment 1 of the present invention.
Figure 13:
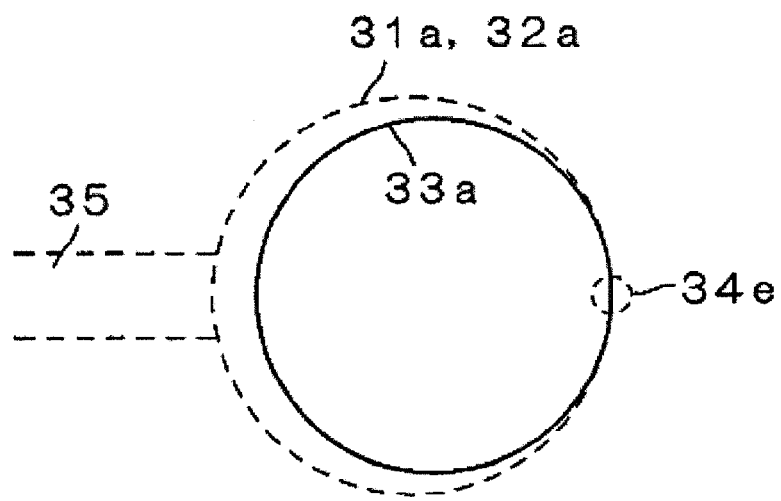
FIG. 13 is a plan view of main parts in the sensor of the blood test apparatus according to Embodiment 1 of the present invention.

FIG. 12 is a cross-sectional view near storing part 34 of sensor 22 and FIG. 13 is a plan view of storing part 34. In FIG. 12 and FIG. 13, diameter 31g of substrate hole 31a formed in substrate 31 and diameter 32g of spacer hole 32a formed in spacer 32 are about 1.75 millimeters, and diameter 33g of cover hole 33a formed in cover 33 is 1.5 millimeters. The centers of substrate hole 31a and spacer hole 32a are on the same line, and the center of cover hole 33a is in a direction slightly apart from the supply channel 35 side. Further, opposite side 34e of supply channel 35 in substrate hole 31a, spacer hole 32a and cover hole 33a are on the same plane.

According to this configuration, projecting part 33c projecting from supply channel 35 toward the center of storing part 34 is formed in storing part 34. The dimension of projection of this projecting part 33c is about 0.25 millimeters and is greater 0.1 millimeters than the sum, 0.15 millimeters, of the thicknesses of substrate 31 and spacer 32. Further, opposite side 34e of supply channel 35 in storing part 34 is formed on the same plane. That is, there are the centers of substrate hole 31a and spacer hole 32a in the center of storing part 34 and the center of cover hole 33a on the opposite side of supply channel 35. The relationship between dimensions 31g, 32g and 33g of these holes are that dimension 31g of substrate hole 31a and diameter 32g of spacer hole 32a are equal and diameter 33g of cover hole 33a is smaller than diameter 32g of spacer hole 32a.

Figure 14:
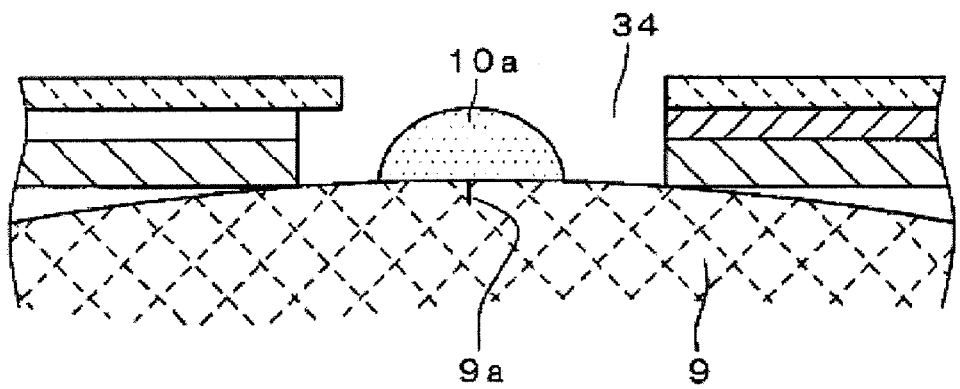
FIG. 14 is a cross-sectional view of the sensor of the blood test apparatus according to Embodiment 1 of the present invention in the first state.
Figure 15:
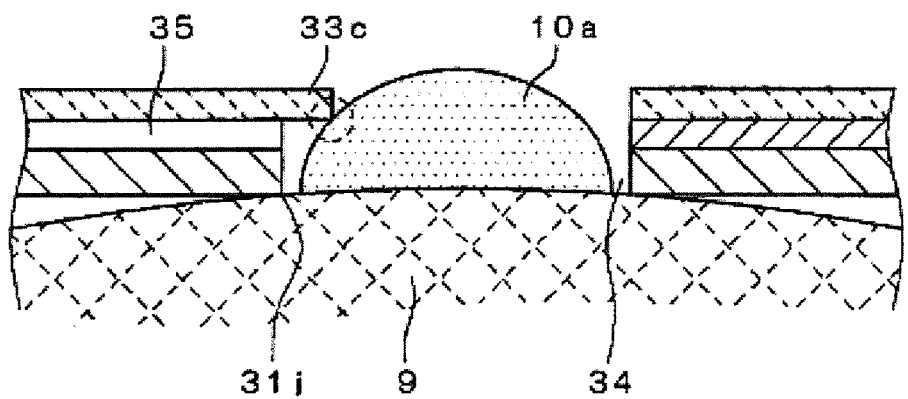
FIG. 15 is a cross-sectional view of the sensor of the blood test apparatus according to Embodiment 1 of the present invention in the second state.
Figure 16:
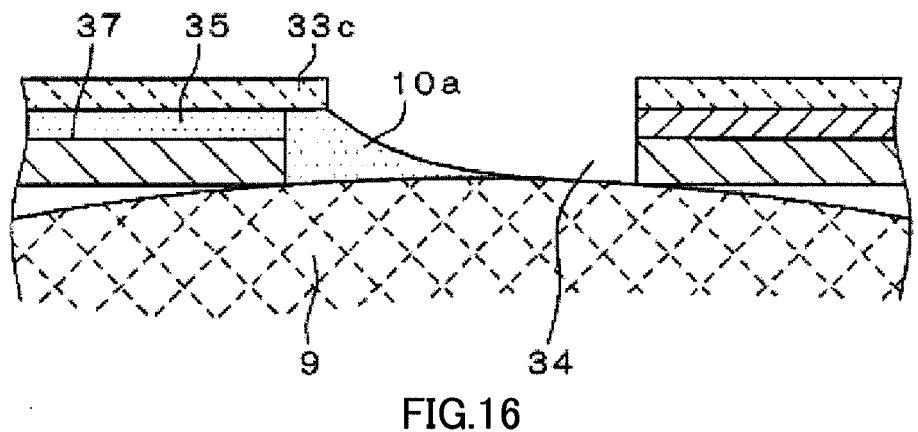
FIG. 16 is a cross-sectional view of the sensor of the blood test apparatus according to Embodiment 1 of the present invention in the third state.

The operation of sensor 22 constituted as described above will be explained below. As shown in FIG. 14, when skin 9 inside storing part 34 is punctured, blood 10 flows out from punctured hole 9a by this puncturing to form blood drop 10a. As shown in FIG. 15, this blood drop 10a increasingly grows, and abuts on the tip of projecting part 33c (shown by the dotted line). Further, before blood drop 10a grows to reach contact point 31j with skin 9 on the supply channel 35 side, as shown in FIG. 16, blood drop 10a flows into detecting section 37 through supply channel 35 at a burst in a rate-controlled state thanks to the capillary action produced by projecting part 33c and skin 9.

In this way, capillary action produced in the space between cover 33 and skin 9 becomes strong on the supply channel 35 side, so that it is possible to allow blood 10 to flow into detecting section 37 through supply channel 35 in a reliable manner before blood 10 fills storing part 34. Consequently, it is possible to reduce the amount of blood left in storing part 34. That is, the amount of blood 10 to sample decreases accordingly, so that it is possible to alleviate the burden upon patients.

Figure 17:
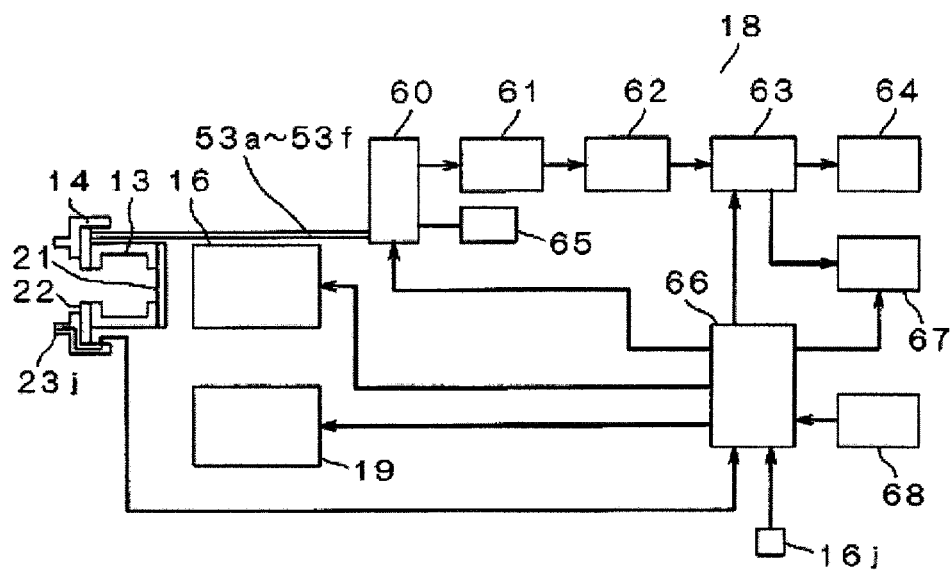
FIG. 17 is a block diagram of an electrical circuit section constituting the blood test apparatus according to Embodiment 1 of the present invention.

FIG. 17 is a block diagram of electrical circuit section 18. In FIG. 17, connection electrodes 41a to 45a and reference electrode 43c of sensor 22 are connected with switching circuit 60 through connectors 53a to 53f. The output of this switching circuit 60 is connected with the input of current/voltage converter 61. The output of current/voltage converter 61 is connected with the input of calculating section 63 through analogue/digital converter 62 (hereinafter "A/D converter"). The output of this calculating section 63 is connected with display section 64 formed with liquid crystal and communication section 67. Further, reference voltage source 65 is connected with switching circuit 60. This reference voltage source 65 may be a ground potential.

Controlling section 66 controls the entire operation of the blood test apparatus according to the present invention. The output of controlling section 66 is connected with laser emitting apparatus 16, the controlling terminal of switching circuit 60, calculating section 63, communication section 67 and vacuuming means 19. Further, the input of controlling section 66 is connected with start button 16j, skin detecting sensors 23j and clock-and-timer 68. It may also be possible to use a vacuum button that is manually pressed, instead of using skin detecting sensors 23j.

Next, the operation of electrical circuit section 18 will be explained. First, to which connectors 53a to 53f connection electrodes 41a to 45a and reference electrode 43c of sensor 22 are connected is detected. That is, according to a command from controlling section 66, a connector having an extremely small electrical resistance between the adjacent connectors compared to other connectors is determined among connectors 53a to 53f. Then, when the connector having an extremely small electrical resistance compared to other connectors is determined, the connector connected with reference electrode 43c is determined as connector 53. It is determined based on connector 53 connected with this reference electrode 43c that connectors 53 (i.e. starting with any of connectors 53a to 53f) are connected with connection electrodes 44a, 45a, 41a, 42a and 43a, respectively. In this way, connectors 53a to 53f respectively connected with connection electrodes 41a to 45a and reference electrode 43c are determined and then blood 10 is measured.

In the measurement operation, switching circuit 60 is switched first to connect detection electrode 41, which serves as an active electrode for measuring the amount of blood components, with current/voltage converter 61. Further, detection electrode 42, which serves as a sensing electrode for sensing the inflow of blood 10, is connected with reference voltage source 65. Then, a certain voltage is applied between detection electrode 41 and detection electrode 42. In this state, when blood 10 flows in, a current flows between detection electrode 41 and detection electrode 42. This current is converted into a voltage by current/voltage converter 61 and this voltage value is converted into a digital value in A/D converter 62. The digital value is outputted to calculating section 63. Calculating section 63 detects based on the digital value that sufficient blood has flowed in. At this point, the operation of vacuuming means 19 is stopped.

Next, glucose, which is a blood component, is measured. To measure the amount of glucose components, according to a command from controlling section 66, switching circuit 60 is switched, and detection electrode 41, which serves as an active electrode for measuring the amount of blood components, is connected with current/voltage converter 61. Further, detection electrode 43, which serves as a counter electrode for measuring the amount of glucose components, is connected with reference voltage source 65.

While, for example, the glucose in blood and its oxidation-reduction enzyme are reacted for a certain period, current/voltage converter 61 and reference voltage source 65 are stopped. Further, after a certain reaction period passes, a voltage is applied between detection electrodes 41 and 43 according to the command from controlling section 66. Then, a current flows between detection electrodes 41 and 43. This current is converted into the voltage in current/voltage converter 61, and the voltage value is converted into a digital value in A/D converter 62 and is outputted to calculating section 63. Calculating section 63 converts this digital value into the amount of glucose components.

Next, after the amount of glucose components is measured, the Hct (hematocrit) value is measured. The Hct value is measured as follows. First, switch circuit 60 is switched according to a command from controlling section 66. Then, detection electrode 45, which serves as the active electrode for measuring the Hct value, is connected with current/voltage converter 61. Further, detection electrode 41, which serves as the counter electrode for measuring the Hct value, is connected with reference voltage source 65.

Next, according to a command from controlling section 66, a certain voltage is applied between detection electrodes 45 and 41 from current/voltage converter 61 and reference voltage source 65. The current flowing between detection electrodes 45 and 41 is converted into the voltage in current/voltage converter 61 and the voltage value is converted into a digital value in A/D converter 62. The digital value is outputted to calculating section 63. Calculating section 63 converts the digital value into an Hct value.

Using the Hct value and the amount of glucose components resulting form this measurement, the amount of glucose components is corrected by the Hct value with reference to a calibration curve or calibration curve table created in advance and the correction result is displayed in display section 64. Further, the correction result may be transmitted from communication section 67 to the injection apparatus that injects insulin. Although a radio wave may be used for this communication, transmission is preferably performed by optical communication that does not interfere with medical equipment.

By transmitting measurement data corrected in this way from communication section 67 to automatically set the dose of insulin to administer in the injection apparatus, the patient needs not to set the dose of insulin to administer, so that annoyance of setting the dose of insulin to administer is eliminated. Further, the dose of insulin can be set in the injection apparatus without an artificial means, so that it is possible to prevent setting errors.

Although measurement of glucose is explained as an example, by replacing sensor 22, the present invention is also effective to measure the lactate acid level, cholesterol and other components in bodily fluid such as blood and interstitial fluid, in addition to glucose.

Figure 18:
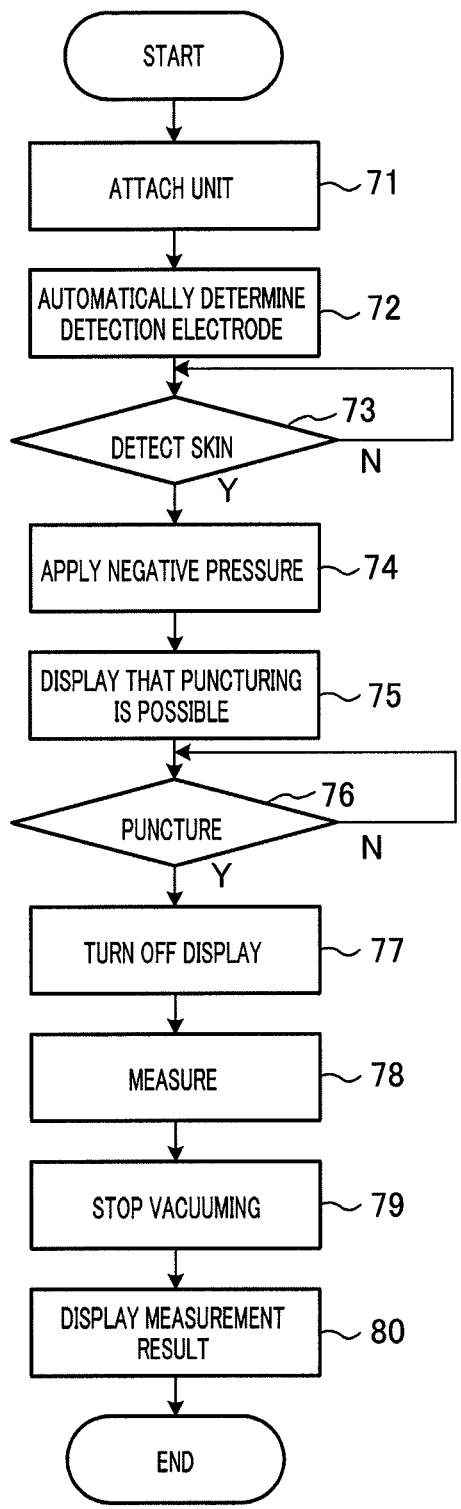
FIG. 18 illustrates the operation of the blood test apparatus according to Embodiment 1 of the present invention.

Next, the operation of blood test apparatus 11 will be explained using FIG. 18. In step 71, filter unit 13 is attached and then sensor unit 14 is attached to cylindrical body 12b. Then, the flow proceeds to step 72. In step 72, by pressing the power supply switch of blood test apparatus 11 or by attaching sensor unit 14 to turn on the power supply switch, power is supplied from battery 20 to electrical circuit section 18. When power is supplied to electrical circuit section 18, reference electrode 43c of sensor 22 is detected first. Based on detection of this reference electrode 43c, detection electrodes 41 to 45 are specified.

Then, in step 73, the patient waits while blood test apparatus 11 is abutted on skin 9 to puncture. When skin detecting sensors 23j of sensor unit 14 detect contact of skin 9, the flow proceeds to step 74 and vacuuming means 56 is operated. Then, this vacuuming means 19 applies a negative pressure to vacuuming chamber 19a (the vicinity of sensor 22). A vacuum button (not shown) may be connected with controlling section 66 and be pressed instead of using skin detecting sensors 23j.

When the current in the vacuum pump forming vacuuming means 19 changes or the time determined in advance in clock-and-timer 68 passes, it is decided that skin 9 inside storing part 34 is sufficiently lifted up, and the flow proceeds to step 75. In step 75, display section 64 displays that puncturing is possible. In next step 76, according to this display, patients press start button 16j constituting laser emitting apparatus 16.

When start button 16j is pressed, laser light 16h passes filter 21 attached to filter unit 13 and punctures skin 9. Blood 10 flows out as a result of puncturing skin 9. This blood 10 is taken in detecting section 37 of sensor 22. Then, in step 78, the blood sugar level of blood 10 is measured.

After the blood sugar level is measured in step 78, the flow proceeds to step 79 and the vacuuming by vacuuming means 19 is stopped. Then, the flow proceeds to step 80 and the blood sugar level that is measured is displayed in display section 64. Further, the display in step 75 to the effect that puncturing is possible, is turned off in step 77. That is, display is turned off at the timing blood 10 reaches detection electrode 42 before the blood sugar level is measured in step 78. Further, the vacuuming may be stopped at this timing.

Embodiment 2

Figure 19:
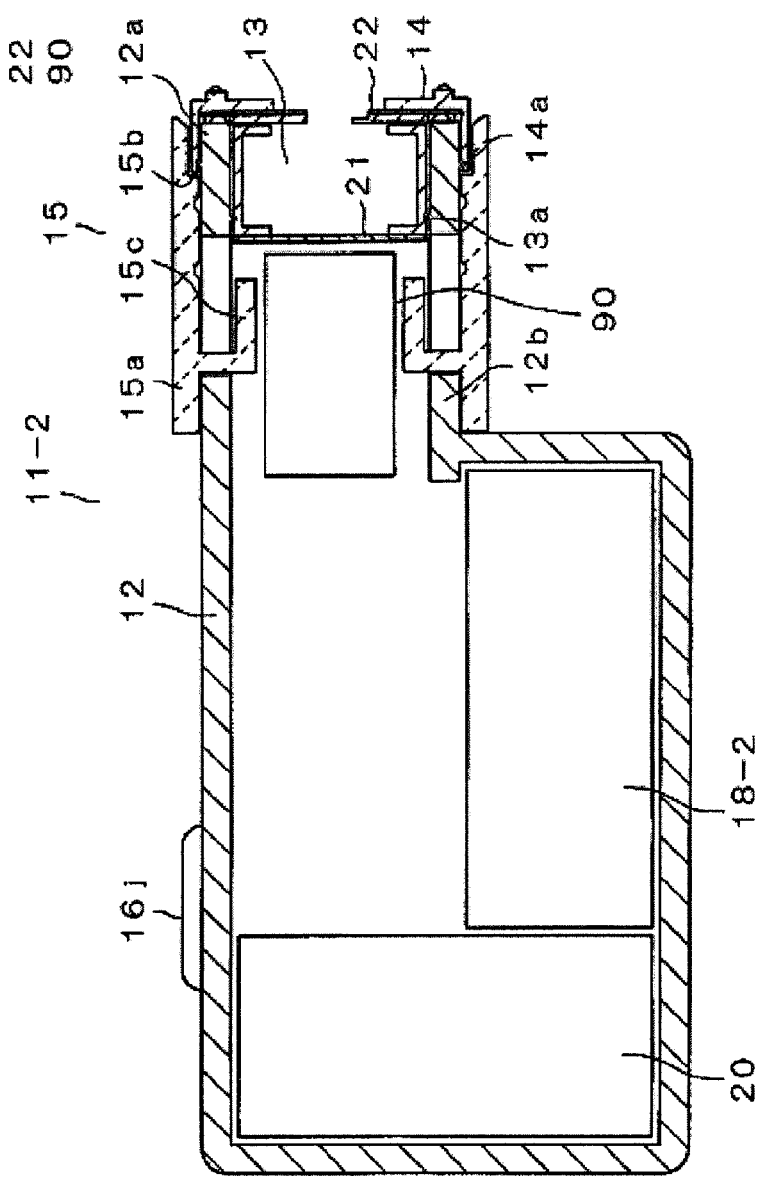
FIG. 19 is a cross-sectional view of the blood test apparatus according to Embodiment 2 of the present invention.

FIG. 19 is a cross-sectional view of blood test apparatus 11-2 according to Embodiment 2 of the present invention. To simplify explanation, the same components as in above-described Embodiment 1 will be assigned the same reference numerals.

In FIG. 19, housing 12 is made of a resinic material and is provided with a cylindrical body of a cylindrical shape that has opening part 12a. Filter unit 13 in which filter 21 is attached is attached inside cylindrical body 12b, and sensor unit 14 in which sensor 22 is attached is attached on the outer surface of cylindrical body 12b.

Body part 15a of ejecting means 15 is provided slidably on the outer surface of cylindrical body 12b. First ejecting part 15b and second ejecting parts 15c are formed in body part 15a. First ejecting part 15b abuts on sensor unit 14 to push out and eject sensor unit 14. Second ejecting parts 15c abut on filter unit 13 to push out and eject filter unit 13.

Next, optical reading section 90 provided in housing 12 will be explained. This optical reading section 90 radiates light on sensor 22 to detect the state of sensor 22 after drops of blood are spotted on sensor 22 and outputs a detection signal according to the amount of received reflected light. Further, electrical circuit section 18-2 is electrically connected with optical reading section 90 that detects the state of sensor 22 and optically reads blood 10 (see FIG. 2) taken in sensor 22 to measure the blood sugar level based on this detection signal. Battery 20 supplies power to electrical circuit section 18-2 and optical reading section 90.

Here, the measurement scheme according to Embodiment 2 is a scheme whereby a custom-designed reagent is added to a sensor such that the sensor shows a unique color matching the blood component to measure and the grade of color showing the specific blood component is optically measured. The same applies to Embodiment 3 described later.

Figure 20:
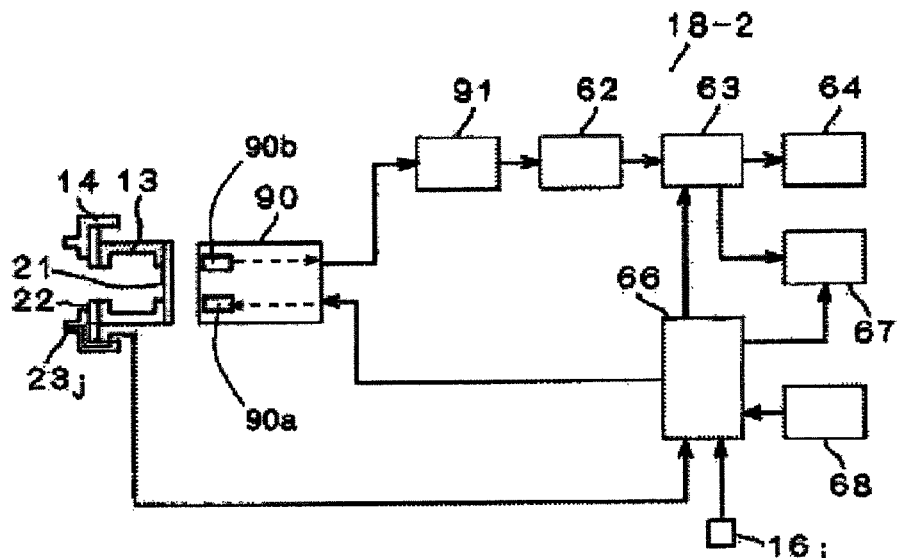
FIG. 20 is a block diagram of the electrical circuit section constituting the blood test apparatus according to Embodiment 2 of the present invention.

FIG. 20 is a block diagram of electrical circuit section 18-2 according to Embodiment 2.

In FIG. 20, as a detecting mechanism for detecting the state of sensor 22 after drops of blood are spotted on sensor 22, optical reading section 90 has light emitting element 90a which radiates light on sensor 22 and light receiving element 90b which receives the light emitted by light emitting element 90a and reflected by sensor 22. Light receiving element 90b outputs an analogue signal matching the amount of received light. This analogue signal is amplified by amplifying section 91. The output of amplifying section 91 is connected to the input of calculating section 63 through A/D converter 62. The output of this calculating section 63 is connected with display section 64 made of liquid crystal and communication section 67.

Controlling section 66 controls the entire operation of the blood test apparatus according to the present invention. The output of controlling section 66 is connected to optical reading section 90, calculating section 63 and communication section 67. Further, the input of controlling section 66 is connected to start button 16j, skin detecting sensors 23j and clock-and-timer 68.

Next, the operation of electrical circuit section 18-2 will be explained.

In a state where drops of blood are spotted on sensor 22 attached in sensor unit 14, in optical reading section 90, light from light emitting element 90a of optical reading section 90 passes filter unit 13 in which filter 21 is attached, is radiated on sensor 22 on which drops of blood are spotted, is reflected by sensor 22 and is received by light receiving element 90b of optical reading section 90. As a result, an analogue signal matching the amount of received light is outputted. The analogue signal outputted is amplified in amplifying section 91 and then is converted into a digital value in A/D converter 62. Then, the digital value is outputted to calculating section 63. Calculating section 63 performs internal arithmetic operation processing based on this digital value and display section 64 displays the measurement result of blood test. Further, the measurement result is transmitted from communication section 67 to the injection apparatus that injects insulin. Although a radio wave may be used for this communication, transmission is preferably performed by optical communication that does not interfere with medical equipment.

Figure 21:
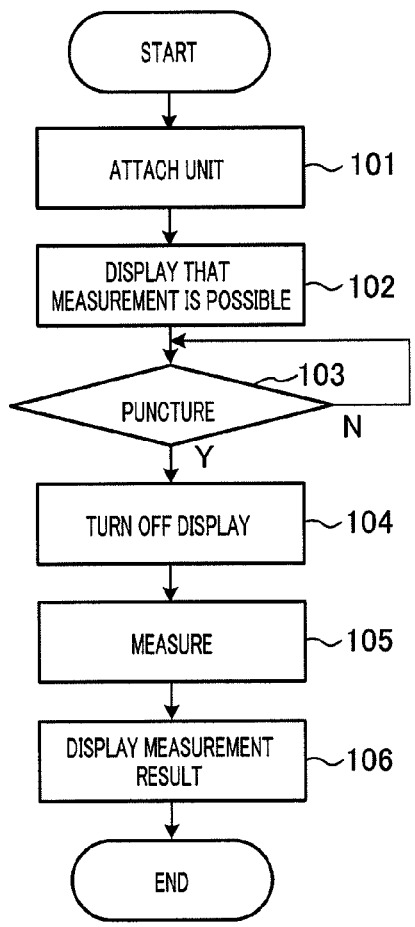
FIG. 21 illustrates the operation of the blood test apparatus according to Embodiment 2 of the present invention.

Next, the operation of blood test apparatus 11-2 according to Embodiment 2 will be explained using FIG. 21. In step 101, filter unit 13 is attached and then sensor unit 14 is attached to cylindrical body 12b. Then, the flow proceeds to step 102. In step 102, by pressing the power supply switch of blood test apparatus 11-2 or by attaching sensor unit 14 to automatically turn on the power supply switch, power is supplied from battery 20 to electrical circuit section 18-2. After power is supplied to electrical circuit section 18-2, preparation for measurement such as initial processing is performed. When the preparation for measurement is finished, display section 64 displays that measurement is possible and stand-by is finished. Next, in step 103, when puncturing skin by means of a separate puncturing apparatus (which is not included in Embodiment 2), the patient waits while sensor 22 attached in sensor unit 14 is abutted on the finger and drops of blood 10 are spotted on sensor 22.

When skin detecting sensors 23j detect contact of the finger, the flow proceeds to step 104 and display is turned off.

At this time, it may also be possible to launch a start of measurement by the method of pressing start button 16j instead of using skin detecting sensors 23j.

Next, the flow proceeds to step 105 and the blood sugar level of blood 10 is measured through the optical reading section. After the blood sugar level is measured in step 105, the flow proceeds to step 106 and the measured blood sugar level is displayed in display section 64.

Embodiment 3

Figure 22:
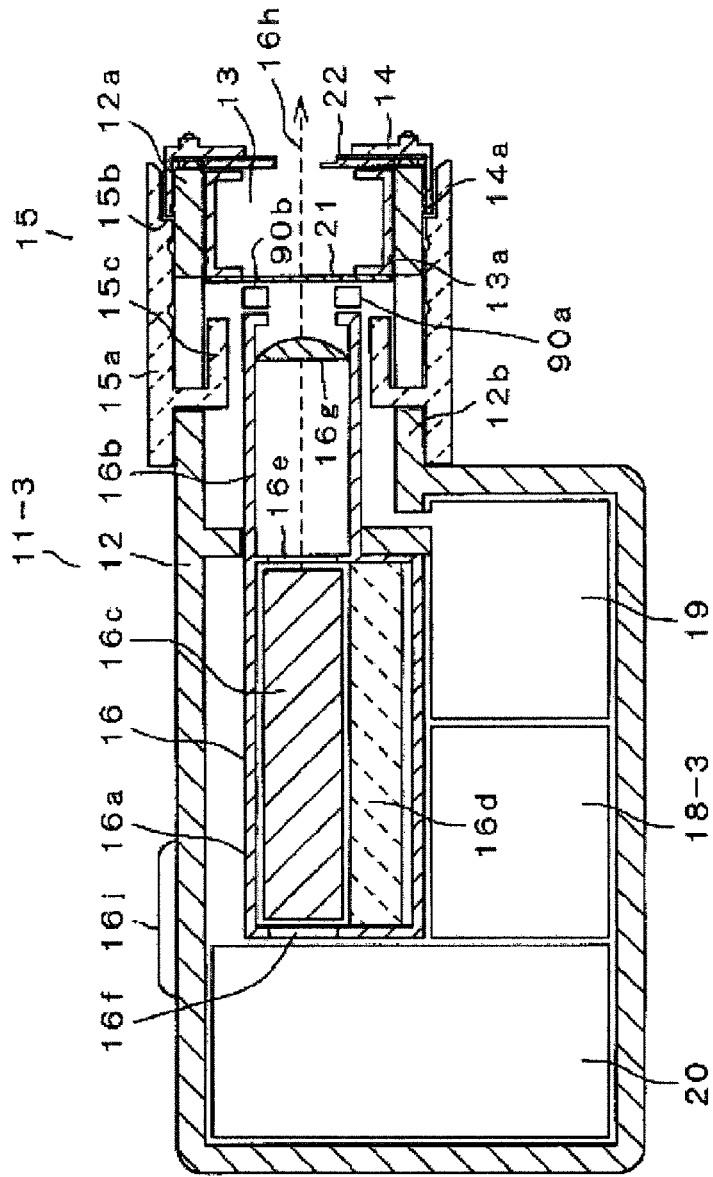
FIG. 22 is a cross-sectional view of the blood test apparatus according to Embodiment 3 of the present invention.

FIG. 22 is a cross-sectional view of blood test apparatus 11-3 according to Embodiment 3 of the present invention. To simplify explanation, the same components as in above-described Embodiment 1 and Embodiment 2 will be assigned the same reference numerals.

In FIG. 22, housing 12 is made of a resinic material and is provided with cylindrical body 12b of a cylindrical shape that has opening part 12a. Filter unit 13 in which filter 21 is attached is attached inside cylindrical body 12b, and sensor unit 14 in which sensor 22 is attached is attached on the outer surface of cylindrical body 12b.

Body part 15a of ejecting means 15 is provided slidably on the outer surface of cylindrical body 12b. First ejecting part 15b and second ejecting parts 15c are formed in body part 15a. First ejecting part 15b abuts on sensor unit 14 to push out and eject sensor unit 14. Second ejecting parts 15c abut on filter unit 13 to push out and eject filter unit 13.

With Embodiment 3, laser emitting apparatus 16 and optical reading section 90 (components 90a and 90b are shown) are provided in housing 12. Laser emitting apparatus 16 is basically the same as the laser emitting apparatus used in above-described Embodiment 1. Further, optical reading section 90 is basically the same as the optical reading section used in above-described Embodiment 2. The function will not be explained.

Figure 23:
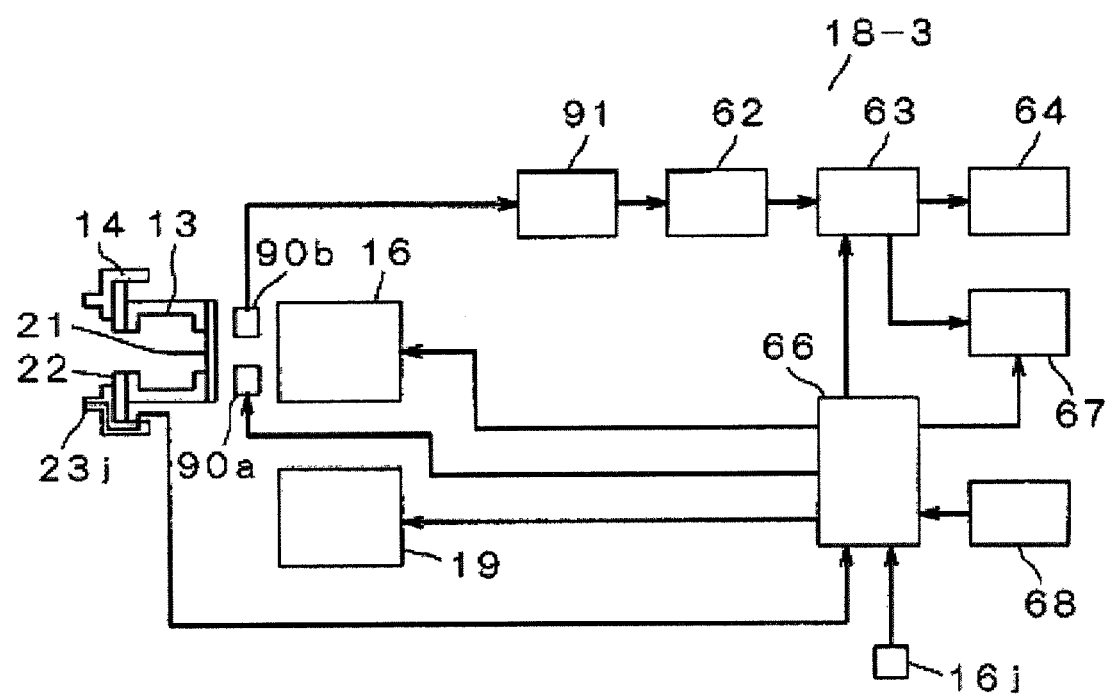
FIG. 23 is a block diagram of the electrical circuit section constituting the blood test apparatus according to Embodiment 3 of the present invention.

FIG. 23 is a block diagram of electrical circuit section 18-3 of blood test apparatus 11-3 according to Embodiment 3.

In FIG. 23, as a detecting mechanism for detecting the state of sensor 22 after drops of blood are spotted on sensor 22, optical reading section 90 has light emitting element 90a which radiates light on sensor 22 and light receiving element 90b which receives the light emitted by light emitting element 90a and reflected by sensor 22. Light receiving element 90b outputs an analogue signal matching the amount of received light. This analogue signal is amplified by amplifying section 91, and then the output of amplifying section 91 is connected to the input of calculating section 63 through analogue/digital converter 62 (hereinafter "A/D converter"). The output of this calculating section 63 is connected with display section 64 made of liquid crystal and communication section 67.

Controlling section 66 controls the entire operation of the blood test apparatus according to the present invention. The output of controlling section 66 is connected to laser emitting apparatus 16, light emitting element 90a which is a component in optical reading section 90, calculating section 63, communication section 67 and vacuuming means 19. Further, the input of controlling section 66 is connected to start button 16j, skin detecting sensors 23j and clock-and-timer 68. Furthermore, it may also be possible to use a vacuum button (not shown) that is manually pressed, instead of using skin detecting sensors 23j.

Next, the operation of electrical circuit section 18-3 will be explained. With the measurement operation, in a state where drops of blood are spotted on sensor 22 attached in sensor unit 14, light from light emitting element 90a of optical reading section 90 passes filter unit 13, is radiated on sensor 22 on which drops of blood are spotted, is reflected by sensor 22 and then is received by light receiving element 90b of optical reading section 90. An analogue signal matching the amount of received light is outputted. The analogue signal outputted is amplified in amplifying section 91 and then is converted into a digital value in A/D converter 62. Then, the digital value is outputted to calculating section 63. Calculating section 63 performs internal arithmetic operation processing based on this digital value and display section 64 displays the measurement result of blood test. Further, the measurement result is transmitted from communication section 67 to the injection apparatus that injects insulin. Although a radio wave may be used for this communication, transmission is preferably performed by optical communication that does not interfere with medical equipment.

Figure 24:
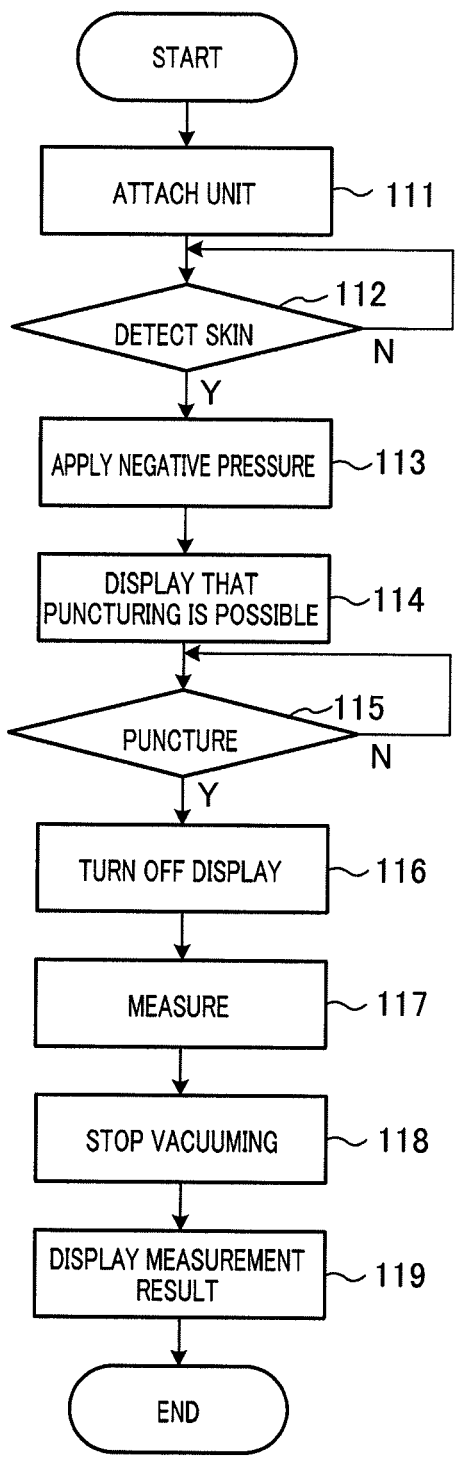
FIG. 24 illustrates the operation of the blood test apparatus according to Embodiment 3 of the present invention.

Next, the operation of blood test apparatus 11-3 according to Embodiment 2 will be explained using FIG. 24. In step 111, filter unit 13 is attached and then sensor unit 14 is attached to cylindrical body 12b. By pressing the power supply switch of blood test apparatus 11-3 or by attaching sensor unit 14 to turn on the power supply switch, power is supplied from battery 20 to electrical circuit section 18-3. After power is supplied to electrical circuit section 18-3, preparation for measurement such as initial processing is performed.

Then, in step 112, the patient waits while blood test apparatus 11-3 is abutted on skin 9 to sample blood. When skin detecting sensors 23j of sensor unit 14 detect skin 9, the flow proceeds to step 113 and vacuuming means 19 is operated. Then, this vacuuming means 19 applies a negative pressure to vacuuming chamber 19a (near sensor 22). Further, it may also be possible to connect a vacuum button (not shown) to controlling section 66 and press this vacuum button, instead of using skin detecting sensors 23j.

When the current in the vacuum pump forming vacuuming means 19 changes or the time determined in advance in clock-and-timer 68 passes, it is decided that skin 9 inside storing part 34 is sufficiently lifted up and the flow proceeds to step 114. In step 114, display section 64 displays that puncturing is possible. In next step 115, according to this display, the patient presses start button 16j constituting laser emitting apparatus 16.

By pressing start button 16j, laser light 16h passes filter 21 attached to filter unit 13 and punctures skin 9. Blood 10 flows out as a result of puncturing skin 9. This blood 10 is taken in detecting section 37 of sensor 22. Then, in step 117, the blood sugar level of blood 10 is measured.

After the blood sugar level is measured in step 117, the flow proceeds to step 118 and the vacuuming by vacuuming means 19 is stopped. Then, the flow proceeds to step 119 and the blood sugar level that is measured is displayed in display section 64.

Further, the display in step 114 to the effect that puncturing is possible, is turned off in step 116. That is, the display is turned off at the timing blood 10 reaches detection electrode 42 before the blood sugar level is measured in step 78. Further, the vacuuming may be stopped at this timing.

The disclosure of Japanese Patent Application No. 2007-007755, filed on Jan. 17, 2007, including the specification, drawings and abstract, is incorporated herein by reference in its entirety.

INDUSTRIAL APPLICABILITY

The blood test apparatus according to the present invention can eject the blood sensor and filter together or separately using a single ejecting means and, consequently, is applicable to blood test apparatuses of an optical measurement type or blood test apparatuses having a puncturing means.

The invention claimed is:

1. A blood test apparatus comprising:
    a housing that comprises an open cylindrical body having a cylindrical shape;
    a sensor unit that includes a blood sensor which analyzes blood and that is detachably attached to the open cylindrical body;
    a filter unit that includes a filter which protects an interior of the housing and that is detachably attached to the open cylindrical body; and
    an ejector that is slidably attached to the open cylindrical body, that moves the sensor unit toward an open side of the open cylindrical body to first push out and eject the sensor unit from the open cylindrical body of the housing and that then moves the filter unit toward the open side of the open cylindrical body to push out and eject the filter unit from the open cylindrical body of the housing,
    wherein the sensor unit comprises a first holder that holds the blood sensor, and the filter unit comprises a second holder that holds the filter, and
    wherein the ejector comprises more than one ejector including a first ejector for ejecting the sensor unit and a second ejector for eject the filter unit,
    the first ejector is configured to abut the first holder to push out the sensor unit, and
    the second ejector is configured to abut the second holder to push out the filter unit.

2. The blood test apparatus according to claim 1, wherein the first ejector and the second ejector are integrally formed.

3. The blood test apparatus according to claim 2, wherein the sensor unit can be replaced while the filter unit is kept attached to the open cylindrical body.

4. The blood test apparatus according to claim 1, wherein:
the housing accommodates a laser emitting apparatus within the housing, the laser emitting apparatus radiates laser light on skin through an interior of the open cylindrical body and punctures the skin;
the filter unit is arranged between the laser emitting apparatus and the sensor unit; and
the filter allows the laser light to pass therethrough.

5. The blood test apparatus according to claim 1, wherein:
the housing accommodates an optical reader within the housing, the optical reader radiates light on skin through an interior of the open cylindrical body and detects an amount of received reflected light;
the filter unit is arranged between the optical reader and the sensor unit; and
the filter allows the light to pass therethrough.

6. The blood test apparatus according to claim 1, wherein:
the housing accommodates therein:
a laser emitting apparatus that radiates laser light on skin through an interior of the open cylindrical body and punctures the skin; and
an optical reader that radiates light on the skin through the interior of the open cylindrical body and detects an amount of received reflected light;
the filter unit is arranged between the laser emitting apparatus and the sensor unit, and between the optical reader and the sensor unit; and
the filter allows the laser light and the light to pass therethrough.

7. The blood test apparatus according to claim 1, wherein the open cylindrical body further comprises a lock that locks the ejector at a time after the sensor unit is ejected and before the filter unit is ejected.

8. The blood test apparatus according to claim 1, further comprising:
a connector that is provided in a front end of the open cylindrical body and that contacts a connection electrode of the blood sensor when the sensor unit is attached to the housing; and
an electrical circuit that connects with the connector and measures components of blood.

9. The blood test apparatus according to claim 8, wherein the ejector comprises a cover that projects from the connector when the sensor unit is ejected.

10. The blood test apparatus according to claim 9, wherein the cover part has a tapered shape.

11. The blood test apparatus according to claim 1, wherein:
the sensor unit comprises a first holder that holds the blood sensor; and
the open cylindrical body comprises a guide that meets the first holder in a part in which the sensor unit is attached.

12. The blood test apparatus according to claim 1, wherein:
the first holder and the second holder comprise transparent members.

13. The blood test apparatus according to claim 1, wherein:
the first holder and the second holder have a cylindrical shape having a cross section which is one of a circle, an oval and a polygon.

14. The blood test apparatus according to claim 1, wherein:
the first holder is water repellant.

15. The blood test apparatus according to claim 1, wherein:
the first holder comprises openings of different diameters on both ends.

16. The blood test apparatus according to claim 1, wherein:
an external shape of the blood sensor is one of a circle and a regular polygon; and
a reference electrode is provided in addition to a detection electrode for an electrode in the blood sensor.

17. The blood test apparatus according to claim 1, wherein the sensor unit comprises a skin detecting sensor that detects skin.

18. The blood test apparatus according to claim 1, wherein:
the blood test apparatus comprises a vacuum provider that applies a negative pressure between the sensor unit and the skin to puncture the skin and that creates a vacuum when the skin detecting sensor detects contact with the skin.

19. The blood test apparatus according to claim 18, wherein the vacuum provider finishes creating the vacuum when an inflow of blood is detected.

20. The blood test apparatus according to claim 1, comprising:
one of a laser emitting apparatus and an optical reader provided within the housing, the laser emitting apparatus radiating laser light on skin through an interior of the open cylindrical body and punctures the skin, the optical reader radiating light on skin through the interior of the open cylindrical body and detects an amount of received reflected light; and
an electrical circuit that is connected to the blood sensor of the sensor unit;
wherein the first holder is detachably attached to the open cylindrical body, and the second holder is detachably attached to the open cylindrical body.

21. The blood test apparatus according to claim 20, wherein the filter unit is arranged opposite to the skin and is recessed further within the cylindrical body than the blood sensor.

22. The blood test apparatus according to claim 20, wherein the filter and the second holder of the filter unit are integral.

23. A blood test apparatus comprising:
a housing that comprises an open cylindrical body having a cylindrical shape;
a sensor unit that includes a blood sensor which analyzes blood and that is detachably attached to the open cylindrical body;
a filter unit that includes a filter which protects an interior of the housing and that is detachably attached to the open cylindrical body; and
an ejector that is slidably attached to the open cylindrical body, that moves the sensor unit toward an open side of the open cylindrical body to first push out and eject the sensor unit from the open cylindrical body of the housing and that then moves the filter unit toward the open side of the open cylindrical body to push out and eject the filter unit from the open cylindrical body of the housing,
wherein the open cylindrical body locks the sensor unit by a first locking part provided in an outer peripheral surface of the open cylindrical body and locks the filter unit by a second locking part provided in an inner peripheral surface of the open cylindrical body.

24. The blood test apparatus according to claim 23, wherein the ejector comprises:
a first lock part that is locked in the first locking part when the sensor unit is ejected; and
a second lock part that is locked in the second locking part when the filter unit is ejected.

* * * * *